(12) United States Patent
Matsunami et al.

(10) Patent No.: US 7,683,220 B2
(45) Date of Patent: Mar. 23, 2010

(54) PROCESS FOR PRODUCTION OF ACROLEIN

(75) Inventors: Etsushige Matsunami, Himeji (JP); Tsukasa Takahashi, Himeji (JP); Hiroto Kasuga, Himeji (JP); Yoshitaka Arita, Nishinomiya (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/225,823

(22) PCT Filed: Mar. 27, 2007

(86) PCT No.: PCT/JP2007/056457
§ 371 (c)(1), (2), (4) Date: Sep. 30, 2008

(87) PCT Pub. No.: WO2007/119528
PCT Pub. Date: Oct. 25, 2007

(65) Prior Publication Data
US 2009/0118549 A1 May 7, 2009

(30) Foreign Application Priority Data
Mar. 30, 2006 (JP) .............. 2006-095024
Mar. 30, 2006 (JP) .............. 2006-095025

(51) Int. Cl.
C07C 45/32 (2006.01)
(52) U.S. Cl. .................. 568/485; 568/486
(58) Field of Classification Search .......... 568/485, 568/486
See application file for complete search history.

(56) References Cited

U.S. PATENT DOCUMENTS

| | | | |
|---|---|---|---|
| 1,916,743 A | 7/1933 | Schwenk et al. |
| 4,093,776 A | 6/1978 | Aoki et al. |
| 4,286,082 A | 8/1981 | Tsubakimoto et al. |
| 4,367,323 A | 1/1983 | Kitamura et al. |
| 4,446,261 A | 5/1984 | Yamasaki et al. |
| 4,625,001 A | 11/1986 | Tsubakimoto et al. |
| 4,683,274 A | 7/1987 | Nakamura et al. |
| 4,873,299 A | 10/1989 | Nowakowsky et al. |
| 4,973,632 A | 11/1990 | Nagasuna et al. |
| 4,985,518 A | 1/1991 | Alexander et al. |
| 5,124,416 A | 6/1992 | Haruna et al. |
| 5,145,906 A | 9/1992 | Chambers et al. |
| 5,244,735 A | 9/1993 | Kimura et al. |
| 5,250,640 A | 10/1993 | Irie et al. |
| 5,264,495 A | 11/1993 | Irie et al. |
| 5,380,808 A | 1/1995 | Sumiya et al. |
| 5,387,720 A | 2/1995 | Neher et al. |
| 5,426,249 A | 6/1995 | Haas et al. |
| 6,174,978 B1 | 1/2001 | Hatsuda et al. |
| 6,194,531 B1 | 2/2001 | Hatsuda et al. |
| 7,396,962 B1 * | 7/2008 | Dubois et al. ........ 568/485 |

FOREIGN PATENT DOCUMENTS

| | | |
|---|---|---|
| EP | 0 811 636 | 12/1997 |
| EP | 0 922 717 | 6/1999 |
| EP | 0 955 086 | 11/1999 |
| FR | 695931 | 12/1930 |
| JP | 6-192147 | 7/1994 |
| JP | 6-211724 | 8/1994 |

* cited by examiner

*Primary Examiner*—Sikarl A Witherspoon
(74) *Attorney, Agent, or Firm*—Wenderoth, Lind & Ponack, L.L.P.

(57) ABSTRACT

There is provided a process for producing acrolein from glycerin, exhibiting a suppressed decrease in the yield of acrolein with time. In the process for producing acrolein by dehydrating glycerin in the presence of a catalyst containing a metal phosphate, one, or two or more, metal phosphates are used, which are selected from aluminum salts, zirconium salts, manganese salts, alkali metal salts (provided that the alkali metal is sodium, potassium, or cesium, and the ratio between the mole number (M) of the alkali metal and the mole number (P) of phosphoric acid (i.e., M/P ratio) in the metal phosphate is 2.0 or lower), alkali earth metal salts (provided that the ratio between the mole number (M) of the alkali earth metal and the mole number (P) of phosphoric acid (i.e., M/P ratio) in the metal phosphate is 1.0 or lower), and the like.

8 Claims, 2 Drawing Sheets

PROCESS FOR PRODUCTION OF ACROLEIN

TECHNICAL FIELD

The present invention relates to a process for the production of acrolein from glycerin, and more specifically, it relates to a process for the production of acrolein, which can exhibit a suppressed decrease in the yield of acrolein with time.

BACKGROUND ART

Biodiesel produced from plant oil has drawn attention not only as a fuel substitution of fossil fuel but also as a substance exhibiting a decrease in carbon dioxide emission, and its demand has been expected to be increased. When the biodiesel fuel is produced, glycerin is produced as a by-product, and therefore, it is needed to use glycerin advantageously.

As one example of utilizing glycerin, there is a process for producing acrolein from glycerin as a starting material. For example, U.S. Pat. No. 1,916,743 discloses a process for producing acrolein by the use of pumice supporting lithium phosphate or copper phosphate as a catalyst, and Japanese Patent Laid-Open Publication No. 6-211724 discloses a process for producing acrolein by the use of a carrier supporting phosphoric acid as a catalyst. Further, French Patent No. 695,931 discloses a process for producing acrolein by the use of silica or alumina supporting lithium phosphate as a catalyst.

In the acrolein production by the use of a catalyst as described above, it is desired to suppress a decrease in the yield of acrolein, even when acrolein is produced by the continued use of a catalyst. If a decrease in the yield of acrolein can be suppressed, it is expected that acrolein derivatives such as acrylic acid, 1,3-propanediol, allyl alcohol, polyacrylic acid, and polyacrylates, which have heretofore been known to be produced from acrolein as a starting material, can be produced at low cost.

DISCLOSURE OF THE INVENTION

In view of the above-described circumstances, it is an object of the present invention to provide a process for the production of acrolein comprising the dehydration of glycerin, which exhibits a suppressed decrease in the yield of acrolein with time.

The present invention is a process for producing acrolein comprising dehydrating glycerin in the presence of a catalyst having a metal phosphate, wherein the metal phosphate is one, or two or more, metal phosphates selected from aluminum salts, zirconium salts, manganese salts, alkali metal salts (provided that the alkali metal is sodium, potassium, or cesium, and the ratio between the mole number (M) of the alkali metal and the mole number (P) of phosphoric acid (i.e., M/P ratio) in the metal phosphate is 2.0 or lower), alkali earth metal salts (provided that the ratio between the mole number (M) of the alkali earth metal and the mole number (P) of phosphoric acid (i.e., M/P ratio) in the metal phosphate is 1.0 or lower), yttrium salts, titanium salts, hafnium salts, vanadium salts, niobium salts, chromium salts, cobalt salts, nickel salts, silver salts, zinc salts, cadmium salts, mercury salts, boron salts, tin salts, lead salts, bismuth salts, lanthanum salts, cerium salts, and samarium salts.

According to the process for the production of acrolein according to the present invention, there can be suppressed a decrease in the yield of acrolein in the dehydration reaction of glycerin.

BEST MODE FOR CARRYING OUT THE INVENTION

The following will describe in detain a process for the production of acrolein according to the present invention. This process is a process for producing acrolein by dehydrating glycerin in the presence of a catalyst for the dehydration of glycerin (hereinafter, "catalyst for the dehydration of glycerin" is referred to simply as "catalyst").

The catalyst is a catalyst for promoting the intramolecular dehydration reaction of glycerin for the production of acrolein. The catalyst contains one, or two or more, specified metal phosphates as catalytic active components.

The above-described metal phosphates are salts of phosphate ions and metal ions, and may be composite phosphates containing two or more phosphates. The phosphate ion is $PO_4^{3-}$, $HPO_4^{2-}$, $H_2PO_4^{-}$, $P_2O_7^{4-}$, $HP_2O_7^{3-}$, $H_2P_2O_7^{2-}$, $H_3P_2O_7^{-}$, or the like. The metal ion is an aluminum ion, a zirconium ion, a manganese ion, an alkali metal ion, an alkali earth metal ion, a yttrium ion, a titanium ion, a hafnium ion, a vanadium ion, a niobium ion, a chromium ion, a cobalt ion, a nickel ion, a silver ion, a zinc ion, a cadmium ion, a mercury ion, a boron ion, a tin ion, a lead ion, a bismuth ion, a lanthanum ion, a cerium ion, or a samarium ion. The above-described alkali metal ion is any of a sodium ion, a potassium ion, or a cesium ion.

In the case where the metal forming the metal phosphate is an alkali metal, for the purpose of achieving a suppressed decrease in the yield of acrolein with time, which is a purpose of the present invention, the M/P ratio between the mole number (M) of the alkali metal and the mole number (P) of phosphoric acid has to be 2.0 or lower. Further, in the case where the metal forming the metal phosphate is an alkali earth metal, the M/P ratio between the mole number (M) of the alkali earth metal and the mole number (P) of phosphoric acid has to be 1.0 or lower. When the ratios exceed these M/P values, either a decrease in the yield of acrolein with time is worse or the yield of acrolein is insufficient to an extent that the metal phosphates cannot be said to be a catalyst. These M/P ratios may preferably be 0.5 or lower in the case of alkali metals, and may preferably be 0.5 or lower, more preferably 0.25 or lower in the case of alkali earth metals. As a method for determining the M/P ratio, the determination can be carried out from the quantitative analysis values of respective elements by fluorescent X-ray analysis.

The metal phosphates are exemplified as follows. Examples of the aluminum salts of phosphoric acid (hereinafter, the "aluminum salts of phosphoric acid" may sometimes be referred to as "AlP") may include $AlPO_4$, $Al_2(HPO_4)_3$, $Al(H_2PO_4)_3$, $Al_4(P_2O_7)_3$, $AlHP_2O_7$, $Al_2(H_2P_2O_7)_3$, and $Al(H_3P_2O_7)_3$. Examples of the zirconium salts of phosphoric acid (hereinafter, the "zirconium salts of phosphoric acid" may sometimes be referred to as "ZrP") may include $Zr(HPO_4)_2$ and $ZrP_2O_7$. Examples of the manganese salts of phosphoric acid may include $MnPO_4$, $Mn_3(PO_4)_2$, $MnHPO_4$, and $Mn(H_2PO_4)_2$. Examples of the alkali metal salts of phosphoric acid may include $Na_2HPO_4$, $NaH_2PO_4$, $Na_4P_2O_7$, $Na_2H_2P_2O_7$, $K_2HPO_4$, $KH_2PO_4$, $K_4P_2O_7$, $K_2H_2P_2O_7$, $Cs_2HPO_4$, $CsH_2PO_4$, $Cs_4P_2O_7$, and $Cs_2H_2P_2O_7$. Examples of the alkali earth metal salts of phosphoric acid may include $MgHPO_4$, $CaHPO_4$, $SrHPO_4$, and $BaHPO_4$.

Although not exemplified above, heretofore known are yttrium salts, titanium salts, hafnium salts, vanadium salts, niobium salts, chromium salts, cobalt salts, nickel salts, silver salts, zinc salts, cadmium salts, mercury salts, boron salts, tin salts, lead salts, bismuth salts, lanthanum salts, cerium salts, and samarium salts of phosphoric acid.

The metal phosphate in the present invention may be preferred to have a crystal structure at least in part thereof. One, or two or more, crystal structures may be mixed in the phosphate. A catalyst containing a metal phosphate with a crystal structure can suppress the deposition of carbonaceous substances on the surface of the catalyst, which are one of deactivation factors of the catalyst.

The crystal structure of the metal phosphate may vary depending on the constituent metals. For example, in the case of $AlPO_4$, which is one of AlP, there are a quartz type, a tridymite type, and a cristobalite type. The tridymite type and the cristobalite type can suppress a decrease in the conversion rate of glycerin, which is one factor of a decrease in the yield of acrolein, and therefore, the tridymite type and the cristobalite type may be preferred. On the other hand, in the case of the quartz type, the adhesion amount of carbonaceous substances is particularly small, and therefore, the quartz type may be preferred. As the adhesion amount of carbonaceous substances is smaller, the easiness of catalyst regeneration by removing the carbonaceous substances can be more highly expected. Further, in the case of ZrP, there are α-ZrP (α-Zr$(HPO_4)_2 \cdot H_2O$), ε-ZrP (ε-Zr$(HPO_4)_2$), pyro-ZrP (crystalline $ZrP_2O_7$), γ-ZrP (γ-Zr$(HPO_4)_2 \cdot H_2O$), γ-ZrP anhydride, β-ZrP (β-Zr$(HPO_4)_2$), and the like, and α-ZrP which can suppress a decrease in the conversion rate of glycerin with time may be preferred.

Further, the following metal phosphate crystals can be recited as examples: hexagonal system crystals for sodium phosphate crystals; orthorhombic system crystals for potassium phosphate crystals; triclinic system crystals, orthorhombic system crystals, and isometric system crystals for barium phosphate crystals; orthorhombic prismatic system crystals for magnesium phosphate crystals; triclinic columnar system crystals for chromium phosphate crystals; orthorhombic columnar system crystals for manganese phosphate crystals; isometric cubic system crystals for silver phosphate crystals; orthorhombic system crystals and triclinic system crystals for zinc phosphate crystals; cristobalite type crystals for boron phosphate crystals; cubic crystals for tin phosphate crystals; hexagonal system crystals for lead phosphate crystals; monoclinic system crystals and hexagonal system crystals for bismuth phosphate crystals; monoclinic system crystals for lanthanum phosphate crystals; and monoclinic system crystals and orthorhombic system columnar crystals for cerium phosphate crystals.

The metal phosphate may be supported on a carrier. It is because the conversion rate of glycerin and the yield of acrolein can be improved by allowing the metal phosphate, which is a catalytic active component, to be supported on a carrier. The amount of the metal phosphate to be supported on a carrier is not particularly limited.

As for the carrier, physical characteristics such as particle size and surface area are not particularly limited. Further, materials are not particularly limited, examples of which may include $SiO_2$, $ZrO_2$, $TiO_2$, $Al_2O_3$, MgO, zeolites, and activated carbon, and $SiO_2$ may be preferred.

The metal phosphate may be any of the commercially available ones, or there may be used a metal phosphate produced by the heretofore known co-precipitation method or precipitation method.

The co-precipitation method or precipitation method is a method for producing a metal phosphate by allowing a phosphate ion such as $PO_4^{3-}$, $HPO_4^{2-}$, $H_2PO_4^-$, $P_2O_7^{4-}$, $HP_2O_7^{3-}$, $H_2P_2O_7^{2-}$, and $H_3O_2O_7$ to coexist with a metal ion. In this connection, as a solvent for allowing a phosphate ion to coexist with a metal ion, water may be preferred, which is economical.

Examples of the starting material to be a source of the phosphate ion may include $H_3PO_4$, $H_4P_2O_7$, and salts of phosphoric acid and ammonia (e.g., $(NH_4)H_2PO_4$, $(NH_4)_2HPO_4$). On the other hand, examples of the starting material to be a source of the metal ion may include nitrates such as $Al(NO_3)_3$, $ZrO(NO_3)_2$, $Mn(NO_3)_2$, $NaNO_3$, $KNO_3$, $CsNO_3$, $Mg(NO_3)_2$, and $Ca(NO_3)_2$; carbonates such as $MnCO_3$, $Na_2CO_3$, $NaHCO_3$, $K_2CO_3$, $KHCO_3$, $Cs_2CO_3$, and $CsHCO_3$; hydroxides such as $Al(OH)_3$, $Mn(OH)_3$, NaOH, KOH, CsOH, and $Mg(OH)_2$; and chlorides such as NaCl, KCl, and CsCl.

In order to allow a metal phosphate to be supported on a carrier, any of the heretofore known methods may be used. For example, an evaporation-to-dryness method, which is one classified in the impregnation methods, may be used. The evaporation-to-dryness method is a method comprising an impregnation step of impregnating a powder carrier or a molded carrier with a liquid containing the metal phosphate starting material (hereinafter, the liquid is referred to the "impregnation liquid"), a drying and fixing step of drying the carrier subjected to the impregnation step and fixing the metal phosphate on the carrier, and a baking step of baking the carrier subjected to the drying and fixing step. Additionally, before the baking step, there may be provided a step of drying the metal phosphate-supported carrier at a temperature of from 100° C. to 200° C. In the evaporation-to-dryness method, the temperature of an impregnation liquid in the impregnation step, although it is not particularly limited, may be not higher than 100° C. and preferably not lower than 30° C., more preferably not lower than 50° C. Although the baking atmosphere in the baking step is not particularly limited, atmospheric air is convenient. Further, the baking temperature of the carrier may usually be from 300° C. to 700° C., preferably 400° C. or higher, and more preferably 500° C. or higher. In the case where the metal phosphate is to be crystallized, the baking temperature may appropriately be set for the crystallization. The baking temperature for this crystallization may be 700° C. or higher.

A catalyst containing a carrier and a metal phosphate with a crystal structure, which is supported on the carrier, can be produced by a method, in which the baking temperature for the evaporation-to-dryness method is not set to be the crystallization temperature of the metal phosphate. The method for its production may be any of the heretofore known methods and, for example, the method may be carried out by mixing a carrier, such as silica, alumina, titania, or zirconia, with a metal phosphate with a crystal structure.

The metal phosphate crystal can be produced by any of the heretofore known production processes. For example, as the processes for production of an AlP crystal and a ZrP crystal, the following production processes are known.

Quartz type AlP is produced through the production of cristobalite type AlP as a meta-stable phase by causing a reaction of aluminum isopropoxide and trimethyl phosphate in the presence of a small amount of water in toluene at 250° C. Tridymite type AlP and cristobalite type AlP can be produced by heating quartz type AlP in atmospheric air to cause the phase transition of the quartz type AlP. The heating temperature of the phase transition of the quartz type to the tridymite type is about 707° C., and the heating temperature of the phase transition of the tridymite type to the cristobalite type is about 1,047° C.

Further, the AlP crystal can be produced as follows. Metavariscite ($AlPO_4.2H_2O$) is prepared from phosphoric acid and aluminum hydroxide. To the metavariscite, an aqueous phosphoric acid solution is added, and the mixture is dried. The dried product is treated with a solvent to produce an AlP crystal. The selection of a solvent to be used in this case makes it possible to selectively produce a quartz type, a tridymite type, and a cristobalite type crystal. When a hydrophilic solvent such as n-butanol is used, quartz type AlP can be produced. When a hydrophobic solvent such as isobutyl methyl ketone is used, cristobalite type AlP can be produced.

α-ZrP can be produced by heating $Zr(HPO_4)_2$ under reflux in from 10 to 15 mol/L of an aqueous phosphoric acid solution. In the case where ZrP with a high crystallinity is produced, it is better to carry out heating under reflux for about 50 hours or longer. Further, α-ZrP can also be produced by a method of heating a mixture of $Zr(HPO_4)_2$ and concentrated phosphoric acid under a reduced pressure (pressure, about 200 mmHg; heating temperature, about 130° C.) with taking distilled water out of the reaction system.

In order to produce ε-ZrP and pyro-ZrP, there may be used a method in which the pressure and heating temperature are changed in the production process of α-ZrP comprising heating a mixture of $Zr(HPO_4)_2$ and concentrated phosphoric acid under a reduced pressure. In this method, when the pressure is adjusted to be about 200 mmHg, ε-ZrP can be obtained by adjusting the heating temperature to be about 180° C. and pyro-ZrP can be obtained by adjusting the heating temperature to about 300° C. In order to produce γ-ZrP and β-ZrP, the hydrothermal reaction of $ZrOCl_2.8H_2O$ and $NaH_2PO_4$ may be carried out.

In the production of acrolein, it may be preferred to select gas-phase dehydration reaction in which a glycerin-containing gas is brought into contact with a catalyst in a reactor selected freely from a fixed bed reactor, a moving bed reactor, a fluidized bed reactor, and the like. The production process of acrolein according to the present invention is not limited to the gas-phase dehydration reaction in which a glycerin-containing gas is brought into contact with a catalyst, but it may be a liquid-phase dehydration reaction in which a glycerin-containing solution is brought into contact with a catalyst.

Glycerin to be used in the glycerin-containing gas may be either of purified glycerin and crude glycerin. The glycerin concentration in the glycerin-containing gas is not particularly limited, but it may be good to be from 0.1 to 100 mol %, preferably 1 mol % or higher, and more preferably 10 mol % or higher at which acrolein can economically be produced with a high efficiency. In the case where it is needed to adjust the glycerin concentration in the glycerin-containing gas, one or more gases selected from steam, nitrogen, air, and the like can be used as a gas for concentration adjustment. Further, in the case where steam is contained in the glycerin-containing gas, a decrease in the activity of a dehydration catalyst can be suppressed and the yield of acrolein can be increased, and therefore, this case may be preferred.

The amount of the glycerin-containing gas in the reactor may be good to be from 100 to 10,000 $hr^{-1}$ in terms of the flow rate (GHSV) of the glycerin-containing gas per unit catalyst volume. It may preferably be 5,000 $hr^{-1}$ or lower, more preferably 3,000 $hr^{-1}$ or lower for the purpose of carrying out the economical production of acrolein with a high efficiency. The temperature for allowing the intramolecular dehydration reaction of glycerin to proceed may be good to be from 200° C. to 500° C., preferably from 250° C. to 450° C., and more preferably from 300° C. to 400° C. The pressure in the dehydration reaction is not particularly limited, so long as it is a pressure within such a range that glycerin is not condensed. It may usually be good to be from 0.001 to 1 MPa, preferably from 0.01 to 0.5 MPa.

The above-described process makes it possible to produce acrolein. The produced acrolein can be used, as having already been heretofore known, as a starting material for the production of acrolein derivatives such as acrylic acid, 1,3-propanediol, methionine, 3-methylproponaldehyde, allyl alcohol, polyacrylic acid, and polyacrylates. Accordingly, the above-described process for the production of acrolein can be incorporated into a process for the production of acrolein derivatives as a matter of course.

For example, acrylic acid is produced by allowing a catalyst and gas of an acrolein-containing composition to coexist in an oxidation reactor selected freely from a fixed bed reactor, a moving bed reactor, a fluidized bed reactor, and the like, and carrying out gas-phase oxidation of acrolein at a temperature of from 200° C. to 400° C.

A catalyst to be used in the oxidation reaction is not particularly limited, so long as it is a catalyst to be used in the case of producing acrylic acid by a catalytic gas-phase oxidation process using molecular oxygen or a gas containing molecular oxygen. Examples of the catalyst may include a mixture of metal oxides such as iron oxide, molybdenum oxide, titanium oxide, vanadium oxide, tungsten oxide, antimony oxide, tin oxide, and copper oxide; and composite products of metal oxides. In these catalysts exemplified, there may be preferred molybdenum-vanadium type catalysts composed mainly of molybdenum and vanadium as constituent metals. Further, the catalyst may be those obtained by allowing the above-described mixture and/or composite product to be supported on a carrier (e.g., zirconia, silica, alumina, and their composite products, and silicon carbide).

The upper limit value of the addition amount of oxygen in the gas of the acrolein-containing composition to be used in the production of acrylic acid is to be appropriately set, because when the addition amount is excess, it may be accompanied with a risk of explosion due to the occurrence of combustion.

In order to recover acrylic acid gas produced by gas-phase oxidation reaction, there is used an absorption tower which can cool or absorb acrylic acid in a solvent such as water.

Since it has heretofore been known that the produced acrylic acid can be used as a starting material for acrylic acid derivatives such as acrylic acid esters and polyacrylic acid, the above-described process for the production of acrylic acid can be the step of acrylic acid production in a process for the production of an acrylic acid derivative.

In the case where polyacrylic acid is produced using the acrylic acid obtained, polyacrylic acid, which can be used as a water-absorbent resin, can be produced by the use of an aqueous solution polymerization method or a reverse-phase suspension polymerization method. In this connection, the aqueous solution polymerization method is a method of polymerizing acrylic acid in an aqueous acrylic acid solution without using a dispersion medium, and it is disclosed in U.S.

Pat. Nos. 4,625,001, 4,873,299, 4,286,082, 4,973,632, 4,985,518, 5,124,416, 5,250,640, 5,264,495, 5,145,906, and 5,380,808, and European Patent Publications Nos. 0 811 636, 0 955 086, and 0 922 717, and the like. Further, the reverse-phase suspension polymerization method is a polymerization method in which an aqueous solution of acrylic acid as a monomer is suspended in a hydrophobic organic solvent, and it is disclosed in U.S. Pat. Nos. 4,093,776, 4,367,323, 4,446,261, 4,683,274, and 5,244,735.

EXAMPLES

The present invention will be explained below more specifically by reference to Examples, but the present invention is not limited to these Examples. The present invention can be put into practice after appropriate modifications or variations within a range meeting the gists described above and later, all of which are included in the technical scope of the present invention.

Using catalysts, acrolein was produced. Details of methods for the preparation of catalysts used in the respective Examples and Comparative Examples and processes for the production of acrolein were as follows.

Example 1

A mixture was prepared by mixing 350 g of ion-exchanged water and 40 g of $SiO_2$ powder under stirring, and the mixture was heated to 80° C. Then, 8.5523 g of $Mn(H_2PO_4)_2 \cdot 4H_2O$ dissolved in a small amount of ion-exchanged water was added to the mixture to make a state that $SiO_2$ was immersed in an immersion liquid (ion-exchanged water containing $Mn(H_2PO_4)_2$). Then, the mixture was heated and stirred at 80° C. until it became just like a paste. The paste-like material was dried at 100° C., and the water content was evaporated to fix P and Mn on a carrier. Thereafter, the P and Mn supported $SiO_2$ was baked in atmospheric air under the conditions of 600° C. and 5 hours to obtain a catalyst. The obtained catalyst was coarsely pulverized and classified to obtain a catalyst having a particle size of from 0.7 to 2.0 mm, which was used as a catalyst in Example 1. The catalyst used in Example 1 was a catalyst containing a silica carrier and manganese phosphate supported on the carrier.

Example 2

A catalyst used in Example 2 was prepared in the same manner as described in Example 1, except that 7.1573 g of $ZrO(NO_3)_2 \cdot 2H_2O$ and 6.1507 g of an aqueous solution containing 85% by mass of $H_3PO_4$ were used in place of $Mn(H_2PO_4)_2 \cdot 4H_2O$ used in Example 1. The catalyst used in Example 2 was a catalyst containing a silica carrier and zirconium phosphate supported on the carrier.

Example 3

A catalyst used in Example 3 was prepared in the same manner as described in Example 1, except that 3.2469 g of $AlPO_4$ was used in place of $Mn(H_2PO_4)_2 \cdot 4H_2O$ used in Example 1. The catalyst used in Example 3 was a catalyst containing a silica carrier and aluminum phosphate supported on the carrier.

Comparative Examples 1 to 4

Catalysts used in Comparative Examples 1 to 4 were prepared in the same manner as described in Example 1, except that $Mn(H_2PO_4)_2 \cdot 4H_2O$ used in Example 1 was relaced as follows. That is, in place of $Mn(H_2PO_4)_2 \cdot 4H_2O$ used in Example 1, 3.0640 g of $(NH_4)H_2PO_4$ was used in Comparative Example 1, 10.1467 g of $Cu_3(PO_2)_3$ was used in Comparative Example 2, 19.8773 g of $Fe_4(P_2O_7)_3$ was used in Comparative Example 3, and 12.8515 g of $Zn_3(PO_4)_2 \cdot 4H_2O$ was used in Comparative Example 4. The catalyst used in Comparative Example 1 was a catalyst containing phosphoric acid supported on a silica carrier. The catalyst used in Comparative Example 2 was a catalyst containing copper phosphate supported on a silica carrier. The catalyst used in Comparative Example 3 was a catalyst containing iron phosphate supported on a silica carrier. The catalyst used in Comparative Example 4 was a catalyst containing zinc phosphate supported on a silica carrier.

Production of Acrolein

Acrolein was synthesized by dehydrating glycerin by the following method using a reactor having a fixed bed of a catalyst. First, a reaction tube made of stainless steel, having an inner diameter of 10 mm and a length of 500 mm, and filled with 15 mL of a catalyst, was prepared as a fixed bed reactor, and this reactor was immersed in a salt bath at 360° C. Then, after nitrogen was allowed to flow into the reactor at a flow rate of 62 mL/min for 30 minutes, glycerin-containing gas (the composition of glycerin-containing gas was 27 mol % glycerin, 34 mol % water, and 39 mol % nitrogen) was allowed to flow into the reactor at a flow rate (GHSV) of 632 $hr^{-1}$. For 30 minutes after a lapse of a prescribed time from the flowing of the glycerin-containing gas into the reactor, the gas flowing from the reactor was absorbed in water, and glycerin and acrolein in the water were quantitatively analyzed. In this analysis, gas chromatography (GC) equipped with FID as a detector was used, and an internal reference method was employed.

From the results obtained by the quantitative analysis using GC, the conversion rate of glycerin (GLY conversion rate) and the yield of acrolein (Acr yield) were calculated. Further, the rate of change of the Acr yield was calculated. The equations for the calculation of the GLY conversion rate, the Acr yield, and the rate of change of the Acr yield are as described by the following equation (1), equation (2), and equation (3).

[Eq. 1]

$$GLY \text{ conversion rate}(\%) = (1 - (\text{quantitative analysis value of glycerin by GC (mol)})/(\text{amount of glycerin flowed into reactor for 30 minutes (mol)})) \times 100 \qquad \text{Equation (1)}$$

[Eq. 2]

$$Acr \text{ yield}(\%) = ((\text{quantitative analysis value of acrolein by GC (mol)})/(\text{amount of glycerin flowed into reactor for 30 minutes (mol)})) \times 100 \qquad \text{Equation (2)}$$

[Eq. 3]

$$\text{Rate of change of } Acr \text{ yield}(\%) = ((Acr \text{ yield for 30 minutes from prescribed flowing time}) - (Acr \text{ yield for flowing time of from 30 to 60 minutes}))/(Acr \text{ yield for flowing time from 30 to 60 minutes}) \times 100 \qquad \text{Equation (3)}$$

The results of acrolein production in Examples 1 to 3 and Comparative Examples 1 to 4 are shown in Table 1.

TABLE 1

| | Catalyst composition (excluding oxygen atom) | Flowing time (min) | GLY conversion rate (%) | Acr yield (%) | Rate of change of Acr yield (%) |
|---|---|---|---|---|---|
| Example 1 | $Si_5Mn_{0.4}P_{0.4}$ | 30 | 99.7 | 60.6 | — |
| | | 150 | 100 | 64.8 | +6.9 |
| | | 330 | 97.6 | 58.3 | −3.8 |
| Example 2 | $Si_5Zr_{0.2}P_{0.4}$ | 30 | 98.2 | 62.5 | — |
| | | 150 | 91.9 | 55.5 | −11.2 |
| Example 3 | $Si_5Al_{0.2}P_{0.2}$ | 60 | 37.6 | 6.2 | — |
| | | 150 | 47.1 | 7.4 | +19.4 |
| Comparative Example 1 | $Si_5P_{0.2}$ | 30 | 83.6 | 65.7 | — |
| | | 150 | 60.4 | 22.8 | −65.3 |
| Comparative Example 2 | $Si_5Cu_{0.6}P_{0.4}$ | 30 | 96.9 | 53.1 | — |
| | | 150 | 71.1 | 22.6 | −57.4 |
| Comparative Example 3 | $Si_5Fe_{0.8}P_{1.2}$ | 30 | 58.8 | 2.3 | — |
| | | 150 | 57.5 | 2.0 | −13.0 |
| Comparative Example 4 | $Si_5Zn_{0.6}P_{0.4}$ | 30 | 19.3 | 2.3 | — |
| | | 150 | 26.3 | 1.5 | −34.8 |

Flowing time: cumulative time of glycerin-containing gas flowing
GLY: glycerin, Acr: acrolein
Rate of change of Acr yield: rate of change based on Acr yield for flowing time of from 30 to 60 minutes In Table 1, it can be confirmed that the rates of change of the Acr yield in Examples 1 to 3 using a manganese salt, a zirconium salt, or an aluminum salt of phosphoric acid were smaller than those in Comparative Examples 1 and 2. This shows that acrolein can stably be produced, if the rate of change of the Acr yield is low. The catalysts used in Comparative Examples 3 and 4 showed Acr yields of lower than 3%, which was extremely low, and therefore, they cannot be said to be a catalyst which can be used for the intramolecular dehydration of glycerin.

The productions of acrolein in Examples 4 to 11 and Comparative Examples 5 to 7 described below were carried out in the same manner as described above in Examples 1 to 3 and Comparative Examples 1 to 4. The processes for the preparation of catalysts used in Examples 4 to 11 and Comparative Examples 5 to 7 were as follows.

Examples 4 to 6

Immersion liquids were prepared by adding $(NH_4)H_2PO_4$ and $NaNO_3$ to 350 g of ion-exchanged water and dissolving them therein. At that time, the mixing mole ratio of $(NH_4)H_2PO_4$ and $NaNO_3$ was $(NH_4)H_2PO_4:NaNO_3=0.2:0.01$ in Example 4, $(NH_4)H_2PO_4:NaNO_3=0.2:0.02$ in Example 5, and $(NH_4)H_2PO_4:NaNO_3=0.2:0.05$ in Example 6. At a normal temperature, 40 g of silica powder was immersed in the immersion liquids, and P and the alkali metal were fixed on the surface of silica by evaporation to dryness.

Then, catalysts were obtained by baking sodium phosphate supported silica in atmospheric air under the conditions of 600° C. and 5 hours. Further, the catalysts were coarsely pulverized and then classified to obtain catalysts having a particle size of from 0.7 to 2.0 mm, which were used as catalysts in Examples 4 to 6. The prepared catalysts were as follows. The catalyst used in Example 4 was a catalyst containing sodium phosphate supported silica with a M/P of 0.05. The catalyst used in Example 5 was a catalyst containing sodium phosphate supported silica with a M/P of 0.1. The catalyst used in Example 6 was a catalyst containing sodium phosphate supported silica with a M/P of 0.25.

Examples 7 to 10

Catalysts were prepared in the same manner as described in Examples 4 to 6, except that $NaNO_3$ used in Examples 4 to 6 was replaced with $CsH_2PO_4$. The mixing mole ratio of $(NH_4)H_2PO_4$ and $CsH_2PO_4$ was $(NH_4)H_2PO_4:CsH_2PO_4=0.19:0.01$ in Example 7; $(NH_4)H_2PO_4:CsH_2PO_4=0.18:0.02$ in Example 8; $(NH_4)H_2PO_4:CsH_2PO_4=0.15:0.05$ in Example 9; and $(NH_4)H_2PO_4:CsH_2PO_4=0:0.2$ in Example 10. The prepared catalysts were as follows. The catalyst used in Example 7 was cesium phosphate supported silica with a M/P of 0.05. The catalyst used in Example 8 was cesium phosphate supported silica with a M/P of 0.1. The catalyst used in Example 9 was cesium phosphate supported silica with a M/P of 0.2. The catalyst used in Example 10 was cesium phosphate supported silica with a M/P of 1.

Example 11

A catalyst was prepared in the same manner as described in Examples 4 to 6, except that $NaNO_3$ used in Examples 4 to 6 was replaced with $KNO_3$. The mixing mole ratio of $(NH_4)H_2PO_4$ and $KNO_3$ was $(NH_4)H_2PO_4:KNO_3=0.2:0.2$. The catalyst used in Example 11 was potassium phosphate supported silica with a M/P of 1.

Comparative Example 5

A catalyst was prepared in the same manner as described in Examples 4 to 6, except that $(NH_4)H_2PO_4$ and $NaNO_3$ used in Examples 4 to 6 was replaced with $(NH_4)H_2PO_3$. The catalyst used in Comparative Example 5 was a $H_3PO_4$ supported catalyst in which an atom mole ratio was Si:P=5:0.1.

Comparative Example 6

A catalyst was prepared in the same manner as described in Examples 4 to 6, except that the amount of $NaNO_3$ used in Examples 4 to 6 was changed. The mixing mole ratio of $(NH_4)H_2PO_4$ and $NaNO_3$ at that time was $(NH_4)H_2PO_4:NaNO_3=0.2:0.6$. The catalyst used in Comparative Example 6 was sodium phosphate supported silica with a M/P of 3.

Comparative Example 7

A catalyst was prepared in the same manner as described in Examples 7 to 10, except that $CsH_2PO_4$ used in Examples 7 to 10 was replaced with $CsNO_3$. The mixing mole ratio of $(NH_4)H_2PO_4$ and $CsNO_3$ was $(NH_4)H_2PO_4:CsNO_3=0.2:0.6$. The catalyst used in Comparative Example 7 was cesium phosphate supported silica with a M/P of 3.

The results of acrolein productions in Examples 4 to 11 and Comparative Examples 5 to 7 are shown in Table 2.

TABLE 2

| | Catalyst composition (excluding oxygen atom) | M/P | Flowing time (min) | GLY conversion rate (%) | Acr yield (%) | Rate of change of Acr yield (%) |
|---|---|---|---|---|---|---|
| Example 4 | $Si_5P_{0.2}Na_{0.01}$ | 0.05 | 30 | 81.0 | 66.7 | — |
| | | | 150 | 59.1 | 40.0 | −40.0 |
| Example 5 | $Si_5P_{0.2}Na_{0.02}$ | 0.1 | 30 | 100.0 | 64.8 | — |
| | | | 150 | 97.8 | 62.3 | −3.9 |
| Example 6 | $Si_5P_{0.2}Na_{0.05}$ | 0.25 | 30 | 100.0 | 66.0 | — |
| | | | 150 | 100.0 | 43.8 | −33.6 |

TABLE 2-continued

| | Catalyst composition (excluding oxygen atom) | M/P | Flowing time (min) | GLY conversion rate (%) | Acr yield (%) | Rate of change of Acr yield (%) |
|---|---|---|---|---|---|---|
| Example 7 | $Si_5P_{0.2}Cs_{0.01}$ | 0.05 | 30 | 99.6 | 62.0 | — |
| | | | 150 | 96.1 | 62.5 | +0.8 |
| Example 8 | $Si_5P_{0.2}Cs_{0.02}$ | 0.1 | 30 | 100.0 | 62.3 | — |
| | | | 150 | 99.8 | 65.5 | +5.1 |
| Example 9 | $Si_5P_{0.2}Cs_{0.05}$ | 0.2 | 30 | 99.8 | 65.5 | — |
| | | | 150 | 99.4 | 61.6 | −6.0 |
| Example 10 | $Si_5P_{0.2}Cs_{0.2}$ | 1 | 30 | 97.8 | 58.0 | — |
| | | | 150 | 98.1 | 51.0 | −12.0 |
| Example 11 | $Si_5P_{0.2}K_{0.2}$ | 1 | 30 | 94.7 | 48.8 | — |
| | | | 150 | 96.0 | 42.7 | −12.5 |
| Comparative Example 5 | $Si_5P_{0.1}$ | — | 30 | 99.7 | 63.9 | — |
| | | | 150 | 69.0 | 24.3 | −62.0 |
| Comparative Example 6 | $Si_5P_{0.2}Na_{0.5}$ | 3 | 30 | 74.2 | 2.0 | — |
| | | | 150 | 76.2 | 2.0 | 0 |
| Comparative Example 7 | $Si_5P_{0.2}Cs_{0.6}$ | 3 | 30 | 96.2 | 4.8 | — |
| | | | 150 | — | — | — |

M/P: mole number of alkali metal element/mole number of phosphorus element
Flowing time: cumulative time of glycerin-containing gas flowing
GLY: glycerin, Acr: acrolein
Rate of change of Acr yield: rate of change based on Acr yield for flowing time of from 30 to 60 minutes In Table 2, it can be confirmed that the rate of change of the Acr yield in Examples 4 to 11, in which the M/P (the ratio of the mole number M of alkali metal to the mole number P of phosphoric acid in the metal phosphate of catalyst) was 2.0 or lower, was smaller than that that obtained in Comparative Examples 5. Since the catalysts used in Comparative Examples 6 and 7 showed Acr yield of lower than 5%, which was extremely low, and therefore, they cannot be said to be a catalyst which can be used for the intramolecular dehydration of glycerin.

As Examples 12 to 17 and Comparative Example 8, acrolein was produced in the same manner as described in Examples 1 to 3 and Comparative Examples 1 to 4, except the flow rate (GHSV) of the gas containing 80% by mass of glycerin was set to be 640 hr$^{-1}$. In the production of acrolein in Examples 12 to 17 described above, the amounts of carbonaceous substances produced by glycerin dehydration reaction and deposited on the catalysts were confirmed. The confirmation was carried out by carrying out quantitative analysis by GC after lapses of 150, 2,490, and 4,770 minutes from the start of the glycerin-containing gas flowing, interrupting the production of acrolein, taking out the catalysts from the reactor, and measuring the masses of the catalysts. The measurement of mass, which was the same as this one, was carried out after the quantitative analysis by GC after a lapse of 150 minutes in Examples 13 and 14; after the quantitative analysis by GC after lapses of 150 and 1,770 minutes in Example 15; after the quantitative analysis by GC after lapses of 150 and 1,230 minutes in Example 16; and after the quantitative analysis by GC after a lapse of 150 minutes in Example 17.

The processes for the preparation of the catalysts used in Examples 12 to 17 and Comparative Example 8 were as follows.

Example 12

A solution containing 160 g of aluminum nitrate nonahydrate available from Wako Pure Chemical Industries, Ltd., and 800 g of water, was mixed with 49 g of 85% phosphoric acid available from Wako Pure Chemical Industries, Ltd. To this mixture was added dropwise 96.7 g of 28% ammonia water for about 50 minutes. From the beginning of the dropwise addition, white precipitate was produced. After completion of the dropwise addition, the mixture was stirred for 1 hour. Then, the solid material (i.e., the precipitate in the mixture) separated from the mixture by suction filtration was washed. In the washing, the following operation from mixing of water to suction filtration was repeated three times. After the solid material and 800 g of water were mixed, the mixture was stirred for 1 hour and was then allowed to stand still for 1 hour. Thereafter, the solid material was separated by suction filtration. The solid material after the washing was dried overnight in a dry oven at 120° C. under a stream of air. The solid material after the drying was baked in air under the conditions of 1,200° C. and 3 hours. Then, the baked product allowed to pass through a sieve having meshes of from 0.7 to 2.0 mm was used as a catalyst. This catalyst was $AlPO_4$. The catalyst pulverized in an agate mortar was analyzed by powder X-ray diffractometry, and the diffraction peaks of a tridymite type crystal were detected.

A powder X-ray diffractiometer "RINT-TTR III" available from Rigaku Corporation was used for the above-described X-ray diffractiometry, and the analysis was carried out under the following conditions.

Figure 1:
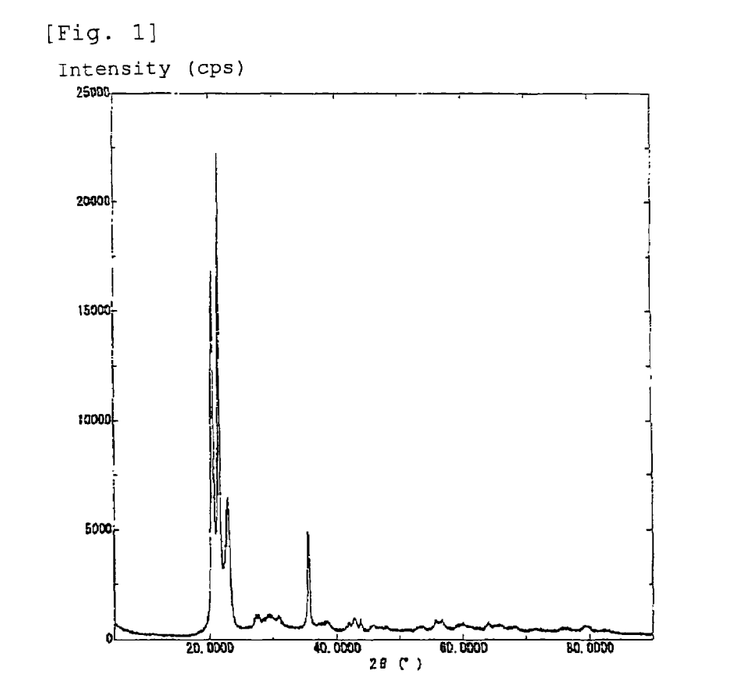
FIG. 1 is a powder X-ray diffraction chart of a catalyst used for the production process of Example 12 according to the present invention.

X-ray source: Cu
Filter: not used
X-ray tube voltage: 50 kV
X-ray tube current: 300 mA
Divergence slit: 1/3°
Scattering slit: 1/2°
Receiving slit: open
Scanning range: from 5° to 90°
Sampling width: 0.02°
Scanning speed: 3.000°/sec The X-ray diffraction peak values of the catalyst used in the production process of Example 12 are shown in Table 3, and the X-ray diffraction chart thereof is shown in FIG. 1.

TABLE 3

| Peak No. | 2θ | Peak search-set width | d value | Intensity | Relative intensity |
|---|---|---|---|---|---|
| 1 | 20.380 | 0.329 | 4.3540 | 10,062 | 79 |
| 2 | 21.500 | 0.259 | 4.1297 | 12,763 | 100 |
| 3 | 22.960 | 0.282 | 3.8703 | 2,853 | 23 |
| 4 | 35.580 | 0.329 | 2.5211 | 2,841 | 23 |

Example 13

First, 66.36 g of water, 38.05 g of an 85% aqueous phosphoric acid solution available from Wako Pure Chemical Industries, Ltd., and 23.40 g of aluminum hydroxide available from Kishida Chemical Co., Ltd., were mixed, and the mixture was stirred at 90° C. for 26 hours. The mixture after the stirring became slurry. Then, the solid material separated from the mixture by filtration was washed with water and ethanol, and then dried at 40° C. under a reduced pressure and further dried overnight under a stream of dry nitrogen. To 17.46 g of a powder obtained by the drying was added 36.9 g of an aqueous solution containing 0.98% by mass of phosphoric acid, followed by stirring, and the mixture was dried at 40° C. for 3 days, to which 150 mL of isobutyl methyl ketone was added, followed by mixing, and thereafter, the mixture was dry distilled for 8 hours. In the dry distillation, a Dean- Stark apparatus was used. During the dry distillation, azeotropic water collected in the Dean-Stark apparatus was discharged. The solid material separated by filtration from the slurry after the dry distillation was washed with ethanol and washed with water and further washed with ethanol, followed by drying, to obtain a powder. The powder was baked under the conditions of 400° C. and 3 hours. The baked product was filled in the inside of a cylinder made of vinyl chloride having an inner diameter of 4 cm and a height of 5 mm, and then pressurized at a pressure of 20 t to form the baked product into a disk shape. The disk-shaped baked product was pulverized, and the baked product, which was allowed to pass through a sieve having meshes of from 0.7 to 2.0 mm, was used as a catalyst. The catalyst was $AlPO_4$. The catalyst pulverized in an agate mortar was analyzed by powder X-ray diffractiometry, and the diffraction peaks of a cristobalite type crystal were detected.

Figure 2:
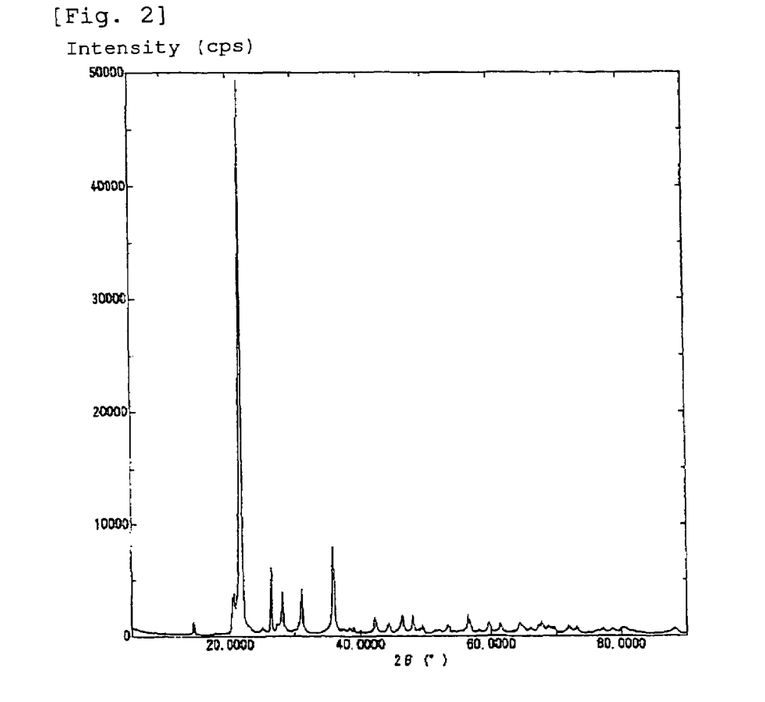
FIG. 2 is a powder X-ray diffraction chart of a catalyst used for the production process of Example 13 according to the present invention.

The X-ray diffraction peak values of the catalyst used in the production process of Example 13 are shown in Table 4, and the X-ray diffractiometry chart thereof is shown in FIG. 2.

TABLE 4

| Peak No. | 2θ | Peak search-set width | d value | Intensity | Relative intensity |
|---|---|---|---|---|---|
| 1 | 14.460 | 0.188 | 6.1205 | 710 | 3 |
| 2 | 20.480 | 0.212 | 4.3330 | 1,620 | 6 |
| 3 | 20.720 | 0.165 | 4.2833 | 1,914 | 7 |
| 4 | 21.720 | 0.282 | 4.0883 | 31,654 | 100 |
| 5 | 26.380 | 0.188 | 3.3757 | 4,320 | 14 |
| 6 | 27.260 | 0.212 | 3.2687 | 384 | 2 |
| 7 | 28.180 | 0.235 | 3.1641 | 2,282 | 8 |
| 8 | 31.080 | 0.259 | 2.8751 | 2,543 | 9 |
| 9 | 35.760 | 0.259 | 2.5089 | 5,557 | 18 |
| 10 | 39.000 | 0.165 | 2.3076 | 375 | 2 |
| 11 | 42.200 | 0.329 | 2.1397 | 921 | 3 |
| 12 | 44.140 | 0.141 | 2.0500 | 434 | 2 |
| 13 | 44.380 | 0.165 | 2.0395 | 426 | 2 |
| 14 | 46.500 | 0.259 | 1.9513 | 974 | 4 |
| 15 | 48.100 | 0.306 | 1.8901 | 960 | 4 |
| 16 | 49.640 | 0.165 | 1.8350 | 488 | 2 |
| 17 | 53.580 | 0.259 | 1.7090 | 443 | 2 |
| 18 | 56.560 | 0.188 | 1.6258 | 1,129 | 4 |
| 19 | 56.820 | 0.141 | 1.6190 | 428 | 2 |
| 20 | 59.500 | 0.165 | 1.5523 | 510 | 2 |
| 21 | 59.740 | 0.165 | 1.5466 | 497 | 2 |
| 22 | 61.400 | 0.259 | 1.5087 | 466 | 2 |
| 23 | 64.320 | 0.141 | 1.4471 | 406 | 2 |
| 24 | 64.420 | 0.259 | 1.4451 | 502 | 2 |
| 25 | 64.920 | 0.212 | 1.4352 | 303 | 1 |
| 26 | 67.100 | 0.141 | 1.3938 | 323 | 2 |
| 27 | 67.360 | 0.165 | 1.3890 | 410 | 2 |
| 28 | 67.780 | 0.188 | 1.3814 | 643 | 3 |
| 29 | 68.940 | 0.165 | 1.3610 | 301 | 1 |
| 30 | 71.900 | 0.282 | 1.3121 | 363 | 2 |

Example 14

First, 66.36 g of water, 38.05 g of an 85% aqueous phosphoric acid solution available from Wako Pure Chemical Industries, Ltd., and 23.40 g of aluminum hydroxide available from Kishida Chemical Co., Ltd., were mixed, and the mixture was stirred at 90° C. for 26 hours. The mixture after the stirring became slurry. Then, the solid material separated from the mixture by filtration was washed with water and ethanol, and then dried at 40° C. under a reduced pressure and further dried overnight under a stream of dry nitrogen. To 17.46 g of a powder obtained by the drying was added 369 g of an aqueous solution containing 0.98% by mass of phosphoric acid, followed by stirring, and the mixture was dried at 40° C. for 3 days, to which 150 mL of n-butanol was added, followed by mixing, and thereafter, the mixture was dry distilled for 8 hours. In the dry distillation, a Dean-Stark apparatus was used. During the dry distillation, azeotropic water collected in the Dean-Stark apparatus was discharged. The solid material separated by filtration from the slurry after the dry distillation was washed with ethanol and washed with water and further washed with ethanol, followed by drying, to obtain a powder. The powder was baked under the conditions of 400° C. and 3 hours. The baked product was filled in the inside of a cylinder made of vinyl chloride having an inner diameter of 4 cm and a height of 5 mm, and then pressurized at a pressure of 20 t to form the baked product into a disk shape. The disk-shaped baked product was pulverized, and the baked product, which was allowed to pass through a sieve having meshes of from 0.7 to 2.0 mm, was used as a catalyst. The catalyst was $AlPO_4$. The catalyst pulverized in an agate mortar was analyzed by powder X-ray diffractiometry, and the diffraction peaks of a cristobalite type crystal were detected.

Figure 3:
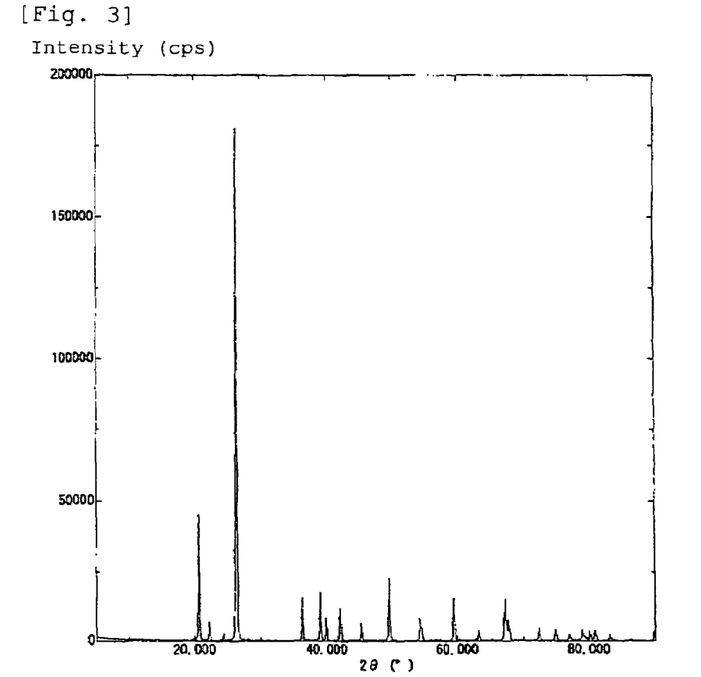
FIG. 3 is a powder X-ray diffraction chart of a catalyst used for the production process of Example 14 according to the present invention.

The X-ray diffraction peak values of the catalyst used in the production process of Example 14 are shown in Table 5, and the X-ray diffractiometry chart thereof is shown in FIG. 3.

TABLE 5

| Peak No. | 2θ | Peak search-set width | d value | Intensity | Relative intensity |
|---|---|---|---|---|---|
| 1 | 20.660 | 0.165 | 4.2956 | 33,429 | 25 |
| 2 | 22.200 | 0.165 | 4.0010 | 5,054 | 4 |
| 3 | 26.340 | 0.165 | 3.3808 | 137,057 | 100 |
| 4 | 36.260 | 0.141 | 2.4754 | 12,809 | 10 |
| 5 | 38.960 | 0.165 | 2.3098 | 15,046 | 11 |
| 6 | 39.920 | 0.165 | 2.2565 | 6,962 | 6 |
| 7 | 42.120 | 0.165 | 2.1436 | 10,088 | 8 |
| 8 | 45.400 | 0.165 | 1.9960 | 5,645 | 5 |
| 9 | 49.600 | 0.165 | 1.8364 | 20,465 | 15 |
| 10 | 54.300 | 0.165 | 1.6880 | 7,330 | 6 |
| 11 | 54.580 | 0.141 | 1.6800 | 3,349 | 3 |
| 12 | 59.460 | 0.165 | 1.5533 | 14,396 | 11 |
| 13 | 63.240 | 0.165 | 1.4692 | 3,510 | 3 |
| 14 | 67.080 | 0.165 | 1.3941 | 9,181 | 7 |
| 15 | 67.320 | 0.141 | 1.3897 | 10,967 | 8 |
| 16 | 67.740 | 0.188 | 1.3821 | 6,509 | 5 |
| 17 | 72.380 | 0.188 | 1.3045 | 4,193 | 4 |
| 18 | 74.940 | 0.165 | 1.2662 | 3,978 | 3 |
| 19 | 78.960 | 0.188 | 1.2115 | 3,956 | 3 |
| 20 | 80.040 | 0.188 | 1.1978 | 2,971 | 3 |
| 21 | 80.840 | 0.188 | 1.1880 | 3,566 | 3 |

Example 15

A catalyst was prepared in the same manner as described in Example 12, except that the baking temperature of 1,200° C. was changed to 600° C. This catalyst was $AlPO_4$. No diffraction peaks of crystal were detected in the X-ray diffraction of this catalyst powder.

Example 16

A powdery baked product was obtained by baking α-ZrP ("CZP-100" available from Daiichi Kigenso Kagaku Kogyo Co., Ltd.) on a porcelain dish in air under the conditions of 500° C. and 1 hour. The baked product was filled in the inside of a cylinder made of vinyl chloride having an inner diameter of 4 cm and a height of 5 mm, and then pressurized at a pressure of 20 t to form the baked product into a disk shape. The disk-shaped baked product was pulverized, and the baked product, which was allowed to pass through a sieve having meshes of from 0.7 to 2.0 mm, was used as a catalyst.

The catalyst was $Zr(HPO_4)_2$. The catalyst was analyzed by powder X-ray diffractometry, and the diffraction peaks of an α-ZrP crystal were detected.

Figure 4:
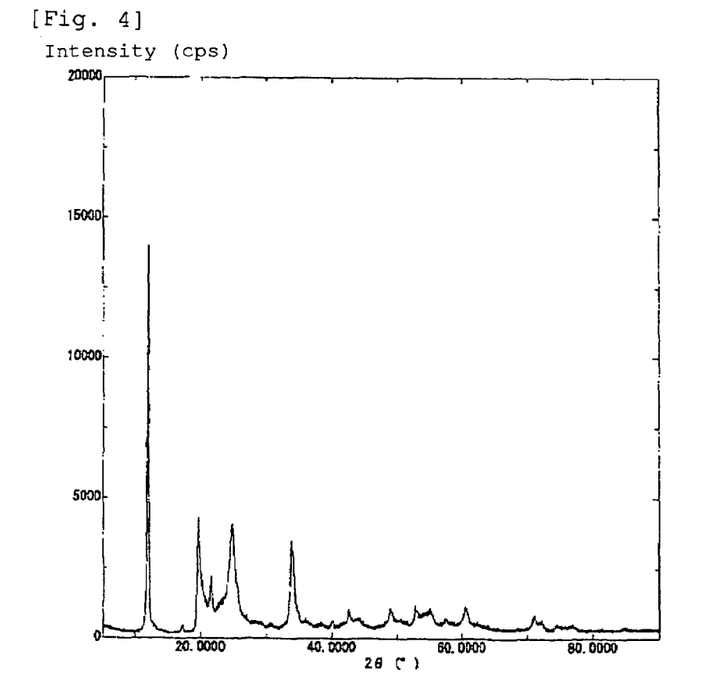
FIG. 4 is a powder X-ray diffraction chart of a catalyst used for the production process of Example 16 according to the present invention.

The X-ray diffraction peak values of the catalyst used in the production process of Example 16 are shown in Table 6, and the X-ray diffractiometry chart thereof is shown in FIG. 4.

TABLE 6

| Peak No. | 2θ | Peak search-set width | d value | Intensity | Relative intensity |
|---|---|---|---|---|---|
| 1 | 11.940 | 0.235 | 7.4060 | 8,670 | 100 |
| 2 | 19.640 | 0.282 | 4.5164 | 2,369 | 28 |
| 3 | 21.500 | 0.259 | 4.1297 | 752 | 9 |
| 4 | 24.740 | 0.165 | 3.5957 | 1,902 | 22 |
| 5 | 24.860 | 0.141 | 3.5786 | 1,663 | 20 |
| 6 | 25.460 | 0.188 | 3.4956 | 391 | 5 |
| 7 | 33.780 | 0.306 | 2.6512 | 1,942 | 23 |
| 8 | 48.880 | 0.165 | 1.8618 | 344 | 4 |
| 9 | 52.740 | 0.306 | 1.7342 | 245 | 3 |
| 10 | 54.980 | 0.212 | 1.6687 | 227 | 3 |
| 11 | 60.560 | 0.188 | 1.5276 | 406 | 5 |

Example 17

First, 500 mL of an aqueous phosphoric acid solution containing 115.3 g of phosphoric acid was added dropwise to a mixture, at 60° C., of 246.2 g of an aqueous zirconium oxynitrate solution ("Zircosol ZN" available from Daiichi Kigenso Kagaku Kogyo Co., Ltd.) and 890 g of water for about 4 hours. From the beginning of the dropwise addition, white precipitate was produced. The mixture after completion of the dropwise addition was stirred for 45 minutes. The solid material (i.e., the precipitate in the mixture) separated from the mixture by suction filtration was washed. In the washing, the following operation from mixing of water to suction filtration was repeated three times. After the solid material and 1,000 g of water were mixed, the mixture was stirred for 1 hour, and then, the solid material was separated by suction filtration. The solid material after the washing was dried overnight in a dry oven at 120° C. under a stream of air. The solid material after the drying was baked under the conditions of 500° C. and 3 hours to obtain a powdery baked product. The baked product was filled in the inside of a cylinder made of vinyl chloride having an inner diameter of 4 cm and a height of 5 mm, and then pressurized at a pressure of 20 t to form the baked product into a disk shape. The disk-shaped baked product was pulverized, and the baked product, which was allowed to pass through a sieve having meshes of from 0.7 to 2.0 mm, was used as a catalyst. The catalyst was $Zr(HPO_4)_2$. The catalyst used in Example 17 had a Zr/P ratio between Zr and P of 1/2, and no clear diffraction peaks were detected in the X-ray diffraction.

Comparative Example 8

A mortar made of porcelain was loaded with 30 g of powder silica ("Carplex FPS-1" available from Shionogi & Co., Ltd.), and a solution containing 1.15 g of ammonium dihydrogen phosphate available from Wako Pure Chemical Industries, Ltd., and 30 g of water. While the liquid in the mortar made of porcelain was mixed, 116 g of water was further added to prepare slurry. The slurry was dried overnight in a dry oven at 120° C. under a stream of air. The dried material was transferred to a porcelain dish and baked in air under the conditions of 600° C. and 5 hours, and the baked product which was sieved was used as a catalyst. The catalyst used in Comparative Example 8 was phosphoric acid supported silica having a Si/P ratio between Si and P of 50/1, and no clear diffraction peaks were detected in the X-ray diffraction of the catalyst.

The production results of acrolein in Examples 12 to 17 and Comparative Example 8 are shown in Table 7. The rate of change of Acr yield in Table 7 is the rate of change based on Acr yield for 30 minutes after 30 minutes from the flowing of glycerin-containing gas.

TABLE 7

| | Catalyst composition | Crystal structure | Flowing time (min) | GLY conversion rate (mol %) | Acr yield (%) | Rate of change of Acr yield (%) | Deposition amount (%) |
|---|---|---|---|---|---|---|---|
| Ex. 12 | $AlPO_4$ | Presence (tridymite) | 30 | 100 | 61.7 | — | — |
| | | | 150 | 100 | 62.8 | +1.8 | 0.39 |
| | | | 330 | 100 | 62.7 | +1.6 | — |
| | | | 1,410 | 100 | 60.8 | −1.5 | — |
| | | | 2,490 | 100 | 62.9 | +1.9 | 2.6 |
| | | | 2,850 | 100 | 61.9 | +0.3 | — |
| | | | 4,290 | 96.3 | 60.3 | −2.3 | — |
| | | | 4,770 | 96.4 | 62.0 | +0.5 | 5.3 |
| Ex. 13 | $AlPO_4$ | Presence (cristobalite) | 30 | 100 | 58.1 | — | — |
| | | | 150 | 100 | 59.4 | +2.2 | 0.55 |
| Ex. 14 | $AlPO_4$ | Presence (quartz) | 30 | 93.2 | 59.1 | — | — |
| | | | 150 | 90.3 | 56.6 | −4.2 | 0.02 |
| Ex. 15 | $AlPO_4$ | None | 30 | 100 | 50.0 | — | — |
| | | | 150 | 100 | 61.0 | +22.0 | 0.60 |
| | | | 330 | 100 | 57.7 | +15.4 | — |
| | | | 1,410 | 97.7 | 60.2 | +20.4 | — |
| | | | 1,770 | 96.0 | 58.6 | +17.2 | 3.8 |
| Ex. 16 | $Zr(HPO_4)_2$ | Presence (α-type) | 30 | 100 | 63.8 | — | — |
| | | | 150 | 100 | 62.8 | −1.6 | 0.26 |
| | | | 330 | 96.3 | 61.9 | −3.0 | — |
| | | | 1,230 | 91.8 | 53.4 | −16.3 | 1.9 |

TABLE 7-continued

|  | Catalyst composition | Crystal structure | Flowing time (min) | GLY conversion rate (mol %) | Acr yield (%) | Rate of change of Acr yield (%) | Deposition amount (%) |
|---|---|---|---|---|---|---|---|
| Ex. 17 | Zr(HPO$_4$)$_2$ | None | 30 | 95.4 | 52.9 | — | — |
|  |  |  | 150 | 88.5 | 46.7 | −11.7 | 0.54 |
| Comp. Ex. 8 | H$_3$PO$_4$/SiO$_2$ | None | 30 | 99.7 | 63.9 | — | — |
|  |  |  | 150 | 69.0 | 24.3 | −62.0 | 0.40 |

Flowing time: cumulative time of glycerin-containing gas flowing
GLY: glycerin, Acr: acrolein
Rate of change of Acr yield: rate of change based on Acr yield for flowing time of from 30 to 60 minutes
Deposition amount: deposition amount of carbonaceous materials In Table 7, in comparison of Examples 12 to 17 with Comparative Example 8, it can be confirmed that the rates of change of the Acr yield in Examples 12 to 17 using the metal phosphates as catalysts showed low decreases.

In Table 7, in comparison of the results after a lapse of 150 minutes in Examples 12 to 14 using the catalysts with crystal structures with the result after a lapse of 150 minutes in Example 15 using the catalyst without any crystal structure, it can be confirmed that the deposition amount of carbonaceous substances was small in Examples 12 to 14. In the Examples 12 and 13 using the catalyst with a tridymite type crystal structure and the catalyst with a cristobalite type crystal structure, respectively, it can be confirmed that the conversion rates of glycerin were higher than that obtained in Example 14 using the catalyst with a quartz type crystal structure. As compared with Example 15 using the catalyst without any crystal structure, it can be confirmed that the rate of change of the Acr yield was low and in addition the deposition amount of carbonaceous substances was low in Example 14. The tendency that the deposition amount of carbonaceous substances was low by using the catalysts with crystal structures is observed in the same manner in comparison of the results after a lapse of 150 minutes in Example 16 using the catalyst with the crystal structure with the results after a lapse of 150 minutes in Example 17 using the catalyst without any crystal structure. That is, it can be confirmed that in the case of metal phosphates with crystal structures, the deposition of carbonaceous substances on the surfaces of catalysts was suppressed.

Separately from the above-described Examples and Comparative Examples, an acrolein-containing composition was prepared in the same manner as described in Example 8, except that the gas flowing from the fixed bed type reactor was liquefied by cooling and recovered. The liquefied and recovered amount was 94% by mass of the aqueous glycerin solution used. The acrolein-containing composition was quantitatively analyzed by GC equipped with FID (GC-14B available from Shimadzu Corporation; Column, Packed Column ZT-7 available from Shinwa Chemical Industries, Ltd.) to obtain the analysis values of 31.0% by mass of acrolein, 1.3% by mass of phenol, 7.5% by mass of 1-hydroxyacetone, 0.1% by mass of glycerin, and 0.1% by mass of allyl alcohol. Further, as a result of analysis by the Karl Fischer's method, the analysis value of 54% by mass of water was obtained.

The above-described acrolein-containing composition was used to produce acrylic acid as follows. As a fixed bed type oxidation reactor, a reaction tube made of a stainless steel having an inner diameter of 25 mm and a length of 500 mm and filled with 20 mL of a catalyst for the production of acrylic acid was made available, and this reactor was placed into a niter bath at 230° C. Thereafter, an acrolein-containing gas was allowed to flow into the reactor. In this connection, as the acrolein-containing gas was used a mixed gas containing a mixture of 1 part by mass of the acrolein-containing composition and 1.3 parts by mass of water (flow rate, 0.209 g/min.), air (flow rate, 331.4 mL/min.), and nitrogen (flow rate, 31.2 mL/min.). After 24 hours from the beginning of the acrolein gas flowing, the gas flowing from the reactor was liquefied by cooling and recovered to obtain an acrylic acid-containing composition.

The above-described catalyst for the production of acrylic acid was a catalyst produced as follows. After 350 g of ammonium paramolybdate, 116 g of ammonium metavanadate, and 44.6 g of ammonium paratungstate were dissolved in 2,500 mL of water which was being heated under stirring, 1.5 g of vanadium trioxide was added. Separately, after 87.8 g of copper nitrate was dissolved in 750 mL of water which was being heated under stirring, 1.2 g of cuprous oxide and 29 g of antimony trioxide were added. After these two solutions were mixed, 1,000 mL of spherical α-alumina having a diameter of from 3 to 5 mm as a carrier was added, and the mixture was evaporated to dryness under stirring to obtain a catalyst precursor.

The catalyst precursor was baked at 400° C. for 6 hours to produce the catalyst for the production of acrylic acid. The metal composition supported on the catalyst for the production of acrylic acid was Mo$_{12}$V$_{6.1}$W$_1$Cu$_{2.3}$Sb$_{1.2}$.

The acrolein and acrylic acid in the acrylic acid-containing composition produced were quantitatively analyzed by GC, and the conversion rate of acrolein, the yield of acrylic acid, and the selectivity of acrylic acid were calculated on the basis of the acrolein in the acrolein-containing gas. The conversion rate of acrolein was 64.3%, the yield of acrylic acid was 33.1%, and the selectivity of acrylic acid was 51.5%.

The invention claimed is:

1. A process for production of acrolein, which comprises dehydrating glycerin in the presence of a catalyst containing a metal phosphate, wherein the metal phosphate is one, or two or more, metal phosphates selected from the group consisting of aluminum salts, zirconium salts, manganese salts, alkali metal salts (wherein the alkali metal is sodium, potassium, or cesium, and a ratio between a mole number (M) of the alkali metal and a mole number (P) of phosphoric acid (M/P ratio) in the metal phosphate is 2.0 or lower), alkali earth metal salts (wherein a ratio between a mole number (M) of the alkali earth metal and a mole number (P) of phosphoric acid (M/P ratio) in the metal phosphate is 1.0 or lower), yttrium salts, titanium salts, hafnium salts, vanadium salts, niobium salts, chromium salts, cobalt salts, nickel salts, silver salts, cadmium salts, mercury salts, boron salts, tin salts, lead salts, bismuth salts, lanthanum salts, cerium salts, and samarium salts.

2. The process for production of acrolein according to claim 1, wherein the metal phosphate has a crystal structure.

3. The process for production of acrolein according to claim 1, wherein the metal phosphate is an aluminum phosphate with a crystal structure, and the crystal structure is one, or two or more, types selected from the group consisting of quartz type, tridymite type, and cristobalite type.

4. The process for production of acrolein according to claim 1, wherein the metal phosphate is zirconium phosphate with a crystal structure, and the crystal structure is a α-zirconium phosphate crystal structure.

5. The process for production of acrolein according to claim 1, wherein the M/P ratio in the alkali metal salt and/or the M/P ratio in the alkali earth metal salt are 0.5 or lower.

6. The process for production of acrolein according to claim 1, wherein the metal phosphate is supported on a carrier.

7. The process for production of acrolein according to claim 1, wherein glycerin is dehydrated by gas-phase reaction in which glycerin gas is brought into contact with a catalyst.

8. A process for production of an acrolein derivative, which comprises a step of using the process for production of acrolein according to claim 1.

* * * * *